US007154009B2

(12) United States Patent
Dieterle et al.

(10) Patent No.: US 7,154,009 B2
(45) Date of Patent: Dec. 26, 2006

(54) LONG-TERM OPERATION OF A HETEROGENEOUSLY CATALYZED GAS PHASE PARTIAL OXIDATION OF PROPENE TO ACROLEIN

(75) Inventors: Martin Dieterle, Mannheim (DE); Jochen Petzoldt, Weisenheim am Berg (DE); Klaus Joachim Mueller-Engel, Stutensee (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/961,050

(22) Filed: Oct. 12, 2004

(65) Prior Publication Data
US 2005/0096487 A1 May 5, 2005

Related U.S. Application Data

(60) Provisional application No. 60/515,114, filed on Oct. 29, 2003.

(30) Foreign Application Priority Data

Oct. 29, 2003 (DE) ............................... 103 50 812

(51) Int. Cl.
*C07C 45/35* (2006.01)
(52) U.S. Cl. ........................ 568/476; 568/477; 568/479
(58) Field of Classification Search ................ 568/476, 568/477, 479
See application file for complete search history.

(56) References Cited

U.S. PATENT DOCUMENTS

| 4,438,217 A | 3/1984 | Takata et al. ............... 502/205 |
| 5,821,390 A | 10/1998 | Ruppel et al. .............. 568/470 |
| 6,346,646 B1 | 2/2002 | Watanabe et al. ........... 562/534 |
| 6,525,217 B1 | 2/2003 | Unverricht et al. ......... 562/544 |
| 2004/0150013 A1 | 8/2004 | Ipposhi |

FOREIGN PATENT DOCUMENTS

| DE | 33 00 044 A1 | 7/1983 |
| DE | 199 48 523 A1 | 4/2001 |
| DE | 102 32 748 | 7/2002 |
| EP | 0 169 449 A2 | 1/1986 |
| EP | 0 339 119 A1 | 11/1989 |
| EP | 0 614 872 A1 | 9/1994 |
| EP | 0 700 714 A1 | 3/1996 |
| EP | 0 990 636 A1 | 4/2000 |
| EP | 1 106 598 A2 | 6/2001 |

OTHER PUBLICATIONS

U.S. Appl. No. 10/974,831, filed Oct. 28, 2004, Petzoldt et al.
U.S. Appl. No. 10/961,050, filed Oct. 12, 2004, Dieterle et al.

*Primary Examiner*—Sikarl A. Witherspoon
(74) *Attorney, Agent, or Firm*—Oblon, Spivak, McClelland, Maier & Neustadt, P.C.

(57) ABSTRACT

A process for the long-term operation of a heterogeneously catalyzed gas phase partial oxidation of propene to acrolein, in which the temperature of the fixed catalyst bed is increased over the time and the gas phase partial oxidation is interrupted at least once per calendar year and the gas mixture G consisting of molecular oxygen, inert gas and optionally steam is conducted through the fixed catalyst bed at a temperature of the fixed catalyst bed of from 250 to 550° C.

13 Claims, No Drawings

LONG-TERM OPERATION OF A HETEROGENEOUSLY CATALYZED GAS PHASE PARTIAL OXIDATION OF PROPENE TO ACROLEIN

The present invention relates to a process for the long-term operation of a heterogeneously catalyzed gas phase partial oxidation of propene to acrolein, by conducting a starting reaction gas mixture which comprises propene, molecular oxygen and at least one inert diluent gas through a fixed catalyst bed at elevated temperature whose catalysts are such that their active composition is at least one multimetal oxide which contains the elements molybdenum and/or tungsten and also at least one of the elements bismuth, tellurium, antimony, tin and copper, and by, in order to counteract the deactivation of the fixed catalyst bed, increasing the temperature of the fixed catalyst bed over the time.

Acrolein is a reactive monomer which is significant especially as an intermediate, for example in the preparation of acrylic acid by two-stage heterogeneously catalyzed partial gas phase oxidation of propene. Acrylic acid is suitable as such or in the form of its alkyl esters, for example, for preparing polymers which may find use as adhesives or water-absorbent materials, among other uses.

It is known that acrolein can be prepared on the industrial scale by a process for heterogeneously catalyzed gas phase partial oxidation of propene to acrolein, by conducting a starting reaction gas mixture comprising propene, molecular oxygen and at least one inert diluent gas through a fixed catalyst bed at elevated temperature whose catalysts are such that their active composition is at least one multimetal oxide which contains the elements molybdenum and/or tungsten and also at least one of the elements bismuth, tellurium, antimony, tin and/or copper (cf., for example, EP-A 990636, EP-A 1106598, EP-A 169449, EP-A 700714, DE-A 3300044 and DE-A 19948623).

It is also known that such a process for heterogeneously catalyzed gas phase partial oxidation of propene to acrolein may be operated substantially continuously over prolonged periods over one and the same fixed catalyst bed. However, the fixed catalyst bed loses quality in the course of the operating time. In general, both its activity and the selectivity of target product formation deteriorate (in this document, target product refers to the sum total of acrolein and any acrylic acid formed as a secondary product of value).

In order, despite this, to operate the fixed catalyst beds, whose manufacturing and exchange is comparatively inconvenient and costly, for as long as possible in a reactor charged with them, the prior art attempts in highly differing ways to counteract their aging process.

EP-A 990 636 (for example page 8, lines 13 and 15) and EP-A 1 106 598 (for example page 13, lines 43 to 45) propose the substantial compensation of the reduction in the quality of the fixed catalyst bed by gradually increasing the temperature of the fixed catalyst bed in the course of the operating time under otherwise substantially constant operating conditions, in order to substantially retain the propene conversion in single pass of the reaction gas mixture through the fixed catalyst bed.

In this context, the temperature of the fixed catalyst bed refers to the temperature of the fixed catalyst bed when the partial oxidation process is performed, except in the theoretical absence of a chemical reaction (i.e. without the influence of the heat of reaction). This also applies in this document. In contrast, effective temperature of the fixed catalyst bed refers in this document to the actual temperature of the fixed catalyst bed taking into account the heat of reaction of the partial oxidation. When the temperature of the fixed catalyst bed is not constant along the fixed catalyst bed (i.e. in the case of a plurality of temperature zones), the term temperature of the fixed catalyst bed in this document means the (numerical) average of the temperature along the fixed catalyst bed.

It is significant in the aforementioned context that the temperature of the reaction gas mixture (and thus also the effective temperature of the fixed catalyst bed) passes through a maximum value (known as the hotspot value) when it passes through the fixed catalyst bed. The difference between hotspot value and the temperature of the fixed catalyst bed at the location of the hotspot value is referred to as the hotspot expansion.

A disadvantage of the procedure recommended in EP-A 990 636 and in EP-A 1 106 598 is that, with increasing temperature of the fixed catalyst bed, its aging process is accelerated (for example certain movement processes within the catalysts which contribute to aging proceed more rapidly). This is in particular generally also because hotspot expansion usually rises more steeply than the temperature of the fixed catalyst bed itself with an increase in the temperature of the fixed catalyst bed (cf., for example, page 12, lines 45 to 48 of EP-A 1 106 598 and page 8, lines 11 to 15 of EP-A 990 636). The effective temperature of the fixed catalyst bed therefore usually increases disproportionately in the hotspot region, which additionally promotes the aging of the fixed catalyst bed.

When a maximum value of the temperature of the fixed catalyst bed is attained, the fixed catalyst bed is therefore customarily fully exchanged.

However, a disadvantage of such a complete exchange is that it is comparatively costly and inconvenient. The process for preparing acrylic acid has to be interrupted for a prolonged time and the costs of catalyst preparation are likewise considerable.

Operating modes are therefore desired for processes for heterogeneously catalyzed gas phase partial oxidation of propene to acrolein which are helpful in prolonging the on-stream time of the fixed catalyst bed in the reactor as far as possible.

In this regard, DE-A 102 32 748 recommends, instead of fully exchanging the fixed catalyst bed, only replacing a portion thereof with a fresh catalyst charge.

A disadvantage of this proposal is that even a partial change of the fixed catalyst bed is accompanied by significant cost and inconvenience.

EP-A 169 449 recommends increasing the on-stream time of the fixed catalyst bed by, after operating the fixed catalyst bed for several years, which is accompanied by increases in the temperature thereof of 15° C. and more, interrupting the process for partial oxidation, and, at fixed catalyst bed temperatures of from 380 to 540° C., conducting a gas consisting substantially of air through it, and subsequently continuing the partial oxidation. EP-A 339 119 recommends, with an analogous mode of operation, the use of a gas comprising oxygen and steam.

In this context, inert gases in a gas mixture which is conducted through the fixed catalyst bed under certain conditions refers in this document to those gases of which at least 95 mol %, preferably at least 98 mol %, most preferably at least 99 mol % or 99.5 mol %, remains unchanged when they are conducted through the fixed catalyst bed. Regarding the gas mixture G to be used in accordance with the invention, steam should not be included under the term inert gas. However, a disadvantage of the procedure of EP-A 169 449 is that, up to the point at which the partial oxidation is interrupted, the aging of the fixed catalyst bed continues and is promoted unhindered. The same also applies to EP-A 614 872.

It is an object of the present invention to provide a process for the long-term operation of a heterogeneously catalyzed gas phase partial oxidation of propene to acrolein, in which the catalyst aging is counteracted in a way by which the intensity of the hotspot expansion over time is lower than in the prior art processes.

We have found that this object is achieved by a process for the long-term operation of a heterogeneously catalyzed gas phase partial oxidation of propene to acrolein, by conducting a starting reaction gas mixture which comprises propene, molecular oxygen and at least one inert diluent gas through a fixed catalyst bed at elevated temperature whose catalysts are such that their active composition is at least one multimetal oxide which contains the elements molybdenum and/or tungsten and also at least one of the elements bismuth, tellurium, antimony, tin and copper, and by, in order to counteract the deactivation of the fixed catalyst bed, increasing the temperature of the fixed catalyst bed over the time, which comprises interrupting the gas phase partial oxidation at least once per calendar year and conducting a gas mixture G consisting of molecular oxygen, inert gas and optionally steam through the fixed catalyst bed at a temperature of the fixed catalyst bed of from 250 to 550° C., (preferably from 300° C. to 500° C., more preferably from 350° C. to 450° C. or 300 to 400° C. or 300 to 360° C.).

It is surprising that, when the process according to the invention is employed, long-term operation of a heterogeneously catalyzed gas phase partial oxidation of propene to acrolein is possible, by which the intensity of the hotspot expansion over the time is lower than in the prior art processes. In favorable cases, the intensity of the hotspot expansion over the time remains constant or even decreases. In addition, the selectivity of target product formation usually remains substantially constant over the time and in favorable cases even increases.

Preference is given in accordance with the invention to interrupting the gas phase partial oxidation at least once every nine months or every six months, more preferably at least once per calendar quarter and most preferably at least once per two successive calendar months and at best at least once per calendar month, and conducting a gas mixture G consisting of molecular oxygen, inert gas and optionally steam through the fixed catalyst bed at a temperature of the fixed catalyst bed of from 250 to 550° C.

However, the gas phase partial oxidation will generally be operated continuously for at least one calendar week before it is interrupted in accordance with the invention.

In other words, the passing of the gas mixture G through the fixed catalyst bed will be carried out in the process according to the invention at a temperature of the fixed catalyst bed of from 250 to 550° C. at least once within 7500 or 7000, or 6500 or 6000, preferably at least once within 5500 or 5000 and most preferably at least once within 4000, or 3000 or 2000, or 1500, or 1000, or 500, operating hours of the partial oxidation. Frequent performance of the process according to the invention has an advantageous effect.

Favorably in accordance with the invention, the temperature of the fixed catalyst bed, while the gas mixture G is conducted through in the course of the implementation of the process according to the invention, is kept at a value $T_G$ which corresponds substantially to that temperature $T_V$ of the fixed catalyst bed which it had in the course of operation of the partial oxidation before it was interrupted in order to conduct the gas mixture G through the fixed catalyst bed in accordance with the invention.

In other words, advantageously in accordance with the invention, $T_G=T_V\pm50°$ C., or $T_G=T_V\pm20°$ C., and very particularly advantageously, $T_G=T_V$.

Normally, $T_V$ will be in the range from 250 to 450° C., frequently in the range from 300 to 400° C.

The period $t_G$ over which the gas mixture G is to be conducted through the fixed catalyst bed in the process according to the invention will generally be at least 2 h, frequently from 6 h to 120 h, in many cases from 12 h to 72 h and often from 20 h to 40 h. However, it may also be 10 days and more. The period $t_G$ is normally sufficiently long that the oxygen content in the gas mixture when it leaves the fixed catalyst bed no longer differs from the oxygen content in the gas mixture G when it enters the fixed catalyst bed. In general, a small oxygen content of the gas mixture G will result in a longer duration $t_G$. Increased oxygen contents in the gas mixture G are advantageous in accordance with the invention.

Appropriately from an application point of view, the gas mixture G in the process according to the invention will contain at least 1% by volume or at least 2% by volume, preferably at least 3% by volume and more preferably at least 4% by volume, of oxygen. However the oxygen content of the gas mixture G will generally be $\leq 21\%$ by volume. In other words, a possible gas mixture G is air. Another possible gas mixture G is lean air. This is air depleted of oxygen.

Advantageous in accordance with the invention is lean air which consists of from 3 to 10% by volume, preferably from 4 to 6% by volume, of oxygen, and a remainder of molecular nitrogen. Appropriately in accordance with the invention, the gas mixture G contains substantially no steam. However, the gas mixture G to be used in accordance with the invention may contain up to 0.1% by volume, or up to 0.5% by volume, or up to 1% by volume, of steam. Normally, the steam content of the gas mixture G is $\leq 75\%$ by volume. The inert gas content of the gas mixture G is generally $\leq 95\%$ by volume, usually $\leq 90\%$ by volume.

Gas mixtures G which are suitable in accordance with the invention may thus consist, for example, of from 3 to 20% by volume of molecular oxygen, from 0 to 5% by volume of steam and a remainder of inert gas. Preferred inert gases are $N_2$ and $CO_2$. Useful gas mixtures G for the process according to the invention are in particular all of those recommended in EP-A 169 449 and in EP-A 339 119. All regeneration conditions recommended in EP-A 169 449 may likewise be employed for the process according to the invention.

The amount of the gas mixture G conducted through the fixed catalyst bed in the process according to the invention may be from 5 or 100 to 5 000 l (STP)/l•h, preferably from 20 or 200 to 3 000 l (STP)/l•h. The reference basis is the volume of the overall fixed catalyst bed, i.e. including any sections used which consist exclusively of inert material. High hourly space velocities of gas mixture G have been found to be advantageous.

Suitable multimetal oxide active compositions for the process according to the invention are in particular active multimetal oxides comprising Mo, Bi and Fe. These are in particular the multimetal oxide compositions containing Mo, Bi and Fe disclosed in DE-A 103 44 149 and DE-A 103 44 264.

These are also in particular the multimetal oxide active compositions of the general formula I of DE-A 199 55 176, the multimetal oxide active compositions of the general formula I of DE-A 199 48 523, the multimetal oxide active compositions of the general formulae I, II and III of DE-A 10101695, the multimetal oxide active compositions of the general formulae I, II and III of DE-A 19948248 and the multimetal oxide active compositions of the general formulae I, II and III of DE-A 19955168 and also the multimetal oxide active compositions specified in EP-A 700714.

Also suitable for the fixed catalyst bed to be used in accordance with the invention are the multimetal oxide catalysts comprising Mo, Bi and Fe which are disclosed in the documents DE-A 10046957, DE-A 10063162, DE-C 3338380, DE-A 19902562, EP-A 15565, DE-C 2380765, EP-A 807465, EP-A 279374, DE-A 3300044, EP-A 575897, U.S. Pat. No. 4,438,217, DE-A 19855913, WO 98/24746, DE-A 19746210 (those of the general formula II), JP-A 91/294239, EP-A 293224 and EP-A 700714. This applies in particular to the exemplary embodiments in these documents, and among these particular preference is given to those of EP-A 15565, EP-A 575897, DE-A 19746210 and DE-A 19855913. Particular emphasis is given in this context to a catalyst according to example 1c from EP-A 15565 and also to a catalyst to be prepared in a corresponding manner but having the active composition $Mo_{12}Ni_{6.5}Zn_2Fe_2Bi_1P_{0.0065}K_{0.06}Ox \cdot 10SiO_2$. Emphasis is also given to the exampl having the serial number 3 from DE-A 19855913 (stoichiometry: $Mo_{12}Co_7Fe_3Bi_{0.6}K_{0.08}$ $Si_{1.6}Ox$) as an unsupported hollow cylinder catalyst of geometry 5 mm×3 mm×2 mm or 5 mm×2 mm×2 mm (each external diameter× height×internal diameter) and also to the unsupported multimetal oxide II catalyst according to example 1 of DE-A 19746210. Mention should also be made of the multimetal oxide catalysts of U.S. Pat. No. 4,438,217. The latter is true in particular when these have a hollow cylinder geometry of the dimensions 5.5 mm×3 mm×3.5 mm, or 5 mm×2 mm×2 mm, or 5 mm×3 mm×2 mm, or 6 mm×3 mm×3 mm, or 7 mm×3 mm×4 mm (each external diameter×height×internal diameter). Likewise suitable are the multimetal oxide catalysts and geometries of DE-A 10101695 or WO 02/062737.

Also suitable are example 1 of DE-A 10046957 (stoichiometry: $[Bi_2W_2O_9 \times 2WO_3]_{0.5} \cdot [Mo_{12}Co_{5.6}Fe_{2.94}Si_{1.59}K_{0.08}O_x]_1$) as an unsupported hollow cylinder (ring) catalyst of geometry 5 mm×3 mm×2 mm or 5 mm×2 mm×2 mm (each external diameter×length×internal diameter), and also the coated catalysts 1, 2 and 3 of DE-A 10063162 (stoichiometry: $Mo_{12}Bi_{1.0}Fe_3Co_7Si_{1.6}K_{0.08}$), except as annular coated catalysts of appropriate coating thickness and applied to support rings of geometry 5 mm×3 mm×1.5 mm or 7 mm×3 mm×1.5 mm (each external diameter×length×internal diameter).

A multitude of the multimetal oxide active compositions suitable for the catalysts of the fixed catalyst bed required for the process according to the invention can be encompassed by the general formula I $$Mo_{12}Bi_aFe_bX^1_cX^2_dX^3_eX^4_fO_n \qquad (I)$$

in which the variables are each defined as follows:
$X^1$=nickel and/or cobalt,
$X^2$=thallium, an alkali metal and/or an alkaline earth metal,
$X^3$=zinc, phosphorus, arsenic, boron, antimony, tin, cerium, lead and/or tungsten,
$X^4$=silicon, aluminum, titanium and/or zirconium,
a=from 0.5 to 5,
b=from 0.01 to 5, preferably from 2 to 4,
c=from 0 to 10, preferably from 3 to 10,
d=from 0 to 2, preferably from 0.02 to 2,
e=from 0 to 8, preferably from 0 to 5,
f=from 0 to 10 and
n=a number which is determined by the valency and frequency of the elements in I other than oxygen.

They are obtainable in a manner known per se (see, for example, DE-A 4023239) and are customarily shaped undiluted to give spheres, rings or cylinders or else used in the form of coated catalysts, i.e. preshaped inert support bodies coated with the active composition. It will be appreciated that they may also be used as catalysts in powder form.

In principle, active compositions of the general formula I can be prepared in a simple manner by obtaining a very intimate, preferably finely divided dry mixture having a composition corresponding to their stoichiometry from suitable sources of their elemental constituents and calcining it at temperatures of from 350 to 650° C. The calcination may be effected either under inert gas or under an oxidative atmosphere, for example air (mixture of inert gas and oxygen) and also under a reducing atmosphere (for example mixture of inert gas, $NH_3$, CO and/or $H_2$). The calcination time can be from a few minutes to a few hours and typically decreases with temperature.

Useful sources for the elemental constituents of the multimetal oxide active compositions I are those compounds which are already oxides and/or those compounds which can be converted to oxides by heating, at least in the presence of oxygen.

In addition to the oxides, such useful starting compounds include in particular halides, nitrates, formates, oxalates, citrates, acetates, carbonates, amine complexes, ammonium salts and/or hydroxides (compounds such as $NH_4OH$, $(NH_4)_2CO_3$, $NH_4NO_3$, $NH_4CHO_2$, $CH_3COOH$, $NH_4CH_3CO_2$ and/or ammonium oxalate which decompose and/or can be decomposed on later calcining at the latest to give compounds which are released in gaseous form can be additionally incorporated into the intimate dry mixture).

The starting compounds for preparing the multimetal oxide active compositions I can be intimately mixed in dry or in wet form. When they are mixed in dry form, the starting compounds are advantageously used as finely divided powders and subjected to calcination after mixing and optional compacting. However, preference is given to intimate mixing in wet form. Customarily, the starting compounds are mixed with each other in the form of an aqueous solution and/or suspension. Particularly intimate dry mixtures are obtained in the mixing process described when the starting materials are exclusively sources of the elemental constituents in dissolved form. The solvent used is preferably water. Subsequently, the aqueous composition obtained is dried, and the drying process is preferably effected by spray-drying the aqueous mixture at exit temperatures of from 100 to 150° C.

Typically, the multimetal oxide active compositions of the general formula I are used in the fixed catalyst bed required for the process according to the invention not in powder form, but rather shaped into certain catalyst geometries, and the shaping may be effected either before or after the final calcination. For example, unsupported catalysts can be prepared from the powder form of the active composition or its uncalcined and/or partially calcined precursor composition by compacting to the desired catalyst geometry (for example by tableting or extruding), optionally with the addition of assistants, for example graphite or stearic acid as lubricants and/or shaping assistants and reinforcing agents such as microfibers of glass, asbestos, silicon carbide or potassium titanate. Examples of suitable unsupported catalyst geometries include solid cylinders or hollow cylinders having an external diameter and a length of from 2 to 10 mm. In the case of the hollow cylinder, a wall thickness of from 1 to 3 mm is advantageous. It will be appreciated that the unsupported catalyst can also have spherical geometry, and the spherical diameter can be from 2 to 10 mm.

A particularly advantageous hollow cylinder geometry is 5 mm×3 mm×2 mm (external diameter×length×internal diameter), in particular in the case of unsupported catalysts.

It will be appreciated that the pulverulent active composition or its pulverulent precursor composition which is yet to be calcined and/or partially calcined can also be shaped by applying to preshaped inert catalyst supports. The coating of the support bodies to produce the coated catalysts is generally performed in a suitable rotatable vessel, as disclosed, for example, by DE-A 2909671, EP-A 293859 or EP-A 714700. To coat the support bodies, the powder composition to be applied is advantageously moistened and dried again after application, for example by means of hot air. The coating thickness of the powder composition applied to the support body is advantageously selected within the range from 10 to 1 000 μm, preferably within the range from 50 to 500 μm and more preferably within the range from 150 to 250 μm.

Useful support materials are the customary porous or nonporous aluminum oxides, silicon dioxide, thorium dioxide, zirconium dioxide, silicon carbide or silicates such as magnesium silicate or aluminum silicate. They generally behave substantially inertly with regard to the target reaction on which the process according to the invention in the first reaction stage is based. The support bodies can have a regular or irregular shape, although preference is given to regularly shaped support bodies having distinct surface roughness, for example spheres or hollow cylinders. It is suitable to use substantially nonporous, surface-roughened spherical supports made of steatite (e.g. Steatite C220 from CeramTec) whose diameter is from 1 to 8 mm, preferably from 4 to 5 mm. However, suitable support bodies also include cylinders whose length is from 2 to 10 mm and whose external diameter is from 4 to 10 mm. In the case of rings suitable as support bodies according to the invention, the wall thickness is also typically from 1 to 4 mm. According to the invention, annular support bodies to be used with preference have a length of from 2 to 6 mm, an external diameter of from 4 to 8 mm and a wall thickness of from 1 to 2 mm. Suitable as support bodies according to the invention are in particular rings of the geometry 7 mm×3 mm×4 mm or 5 mm×3 mm×2 mm (external diameter× length×internal diameter). It will be appreciated that the fineness of the catalytically active oxide compositions to be applied to the surface of the support body will be adapted to the desired coating thickness (cf. EP-A 714 700).

Suitable multimetal oxide active compositions for the catalysts of the fixed catalyst bed of the process according to the invention are also compositions of the general formula II

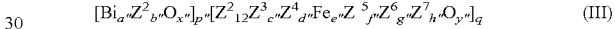  (II)

in which the variables are defined as follows:
$Y^1$=only bismuth or bismuth and at least one of the elements tellurium, antimony, tin and copper,
$Y^2$=molybdenum or molybdenum and tungsten,
$Y^3$=an alkali metal, thallium and/or samarium,
$Y^4$=an alkaline earth metal, nickel, cobalt, copper, manganese, zinc, tin, cadmium and/or mercury,
$Y^5$=iron or iron and at least one of the elements chromium and cerium,
$Y^6$=phosphorus, arsenic, boron and/or antimony, $Y^7$=a rare earth metal, titanium, zirconium, niobium, tantalum, rhenium, ruthenium, rhodium, silver, gold, aluminum, gallium, indium, silicon, germanium, lead, thorium and/or uranium,
a'=from 0.01 to 8,
b'=from 0.1 to 30,
c'=from 0 to 4,
d'=from 0 to 20,
e'=from >0 to 20,
f'=from 0 to 6,
g'=from 0 to 15,
h'=from 8 to 16,
x',y'=numbers which are determined by the valency and frequency of the elements in II other than oxygen and
p,q=numbers whose p/q ratio is from 0.1 to 10, comprising three-dimensional regions of the chemical composition $Y^1_{a'}Y^2_{b'}O_{x'}$ which are delimited from their local environment as a consequence of their different composition from their local environment, and whose maximum diameter (longest line passing through the center of the region and connecting two points on the surface (interface) of the region) is from 1 nm to 100 μm, frequently from 10 nm to 500 nm or from 1 μm to 50 or 25 μm.

Particularly advantageous multimetal oxide compositions II are those in which $Y^1$ is only bismuth.

Among these, preference is given in turn to those of the general formula III

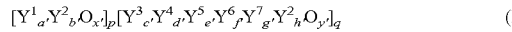  (III)

in which the variables are defined as follows:
$Z^2$=molybdenum or molybdenum and tungsten,
$Z^3$=nickel and/or cobalt,
$Z^4$=thallium, an alkali metal and/or an alkaline earth metal,
$Z^5$=phosphorus, arsenic, boron, antimony, tin, cerium and/or lead,
$Z^6$=silicon, aluminum, titanium and/or zirconium,
$Z^7$=copper, silver and/or gold,
a''=from 0.1 to 1,
b''=from 0.2 to 2,
c''=from 3 to 10,
d''=from 0.02 to 2,
e''=from 0.01 to 5, preferably from 0.1 to 3,
f''=from 0 to 5,
g''=from 0 to 10,
h''=from 0 to 1,
x'',y''=numbers which are determined by the valency and frequency of the elements in III other than oxygen,
p'',q''=numbers whose p''/q'' ratio is from 0.1 to 5, preferably from 0.5 to 2, and very particular preference is given to those compositions III in which $Z^2_{b''}$=(tungsten)$_{b''}$ and $Z^2_{12}$=(molybdenum)$_{12}$.

It is also advantageous when at least 25 mol % (preferably at least 50 mol % and more preferably at least 100 mol %) of the total proportion of $[Y^1_aY^2_bO_x]_p$ ($[Bi_{a''}Z^2_{b''}O_{x''}]_{p''}$) of the multimetal oxide compositions II (multimetal oxide compositions III) suitable according to the invention in the multimetal oxide compositions II (multimetal oxide compositions III) suitable according to the invention are in the form of three-dimensional regions of the chemical composition $Y^1_{a'}Y^2_{b'}O_{x'}$ [$Bi_{a''}Z^2_{b''}O_{x''}$] which are delimited from their local environment as a consequence of their different chemical composition from their local environment, and whose maximum diameter is in the range from 1 nm to 100 μm.

With regard to the shaping, the statements made for the multimetal oxide I catalysts apply to the multimetal oxide II catalysts.

The preparation of multimetal oxide II active compositions is described, for example, in EP-A 575897 and also in DE-A 19855913, DE-A 10344149 and DE-A 10344264.

Appropriately from an application point of view for the process according to the invention, heterogeneously catalyzed gas phase partial oxidation of propene to acrolein may be carried out in a tube bundle reactor charged with the fixed bed catalysts, as described, for example, in EP-A 700 714 or DE-A 4 431 949 or WO 03/057653, or WO 03/055835, or WO 03/059857, or WO 03/076373.

In other words, in the simplest manner, the fixed catalyst bed to be used in the process according to the invention is disposed in the uniformly charged metal tubes of a tube bundle reactor and a heating medium (one-zone method), generally a salt melt, is conducted around the metal tubes. Salt melt (heating medium) and reaction gas mixture may be conducted in simple co- or countercurrent. However, the heating medium (the salt melt) may also be conducted around the tube bundle in a meandering manner viewed over the reactor, so that only viewed over the entire reactor does a co- or countercurrent to the flow direction of the reaction gas mixture exist. The volume flow rate of the heating medium (heat exchange medium) is typically such that the temperature rise (caused by the exothermicity of the reaction) of the heat exchange medium from the inlet point into the reactor to the outlet point from the reactor is from 0 to 10° C., frequently from 2 to 8° C., often from 3 to 6° C. The inlet temperature of the heat exchange medium into the tube bundle reactor (in this document, this corresponds to the temperature of the fixed catalyst bed) is generally from 250 to 450° C., frequently from 300 to 400° C. or from 300 to 380° C. Suitable heat exchange media are in particular fluid heating media. It is particularly appropriate to use melts of salts such as potassium nitrate, potassium nitrite, sodium nitrite and/or sodium nitrate, or of low-melting metals such as sodium, mercury and also alloys of different metals. Ionic liquids can also be used.

Appropriately, the reaction gas mixture is fed to the charge of fixed bed catalyst preheated to the desired reaction temperature.

Especially in the case of the desired high (e.g. $\geq 140$ l (STP)/l·h or $\geq 160$ l (STP)/l·h, but generally $\leq 600$ l (STP)/l·h) final hourly space velocities of propene on the fixed catalyst bed, the process according to the invention is appropriately carried out in a two-zone tube bundle reactor (however, it is likewise possible to carry it out in a one-zone tube bundle reactor). A preferred variant of a two-zone tube bundle reactor which can be used for this purpose in accordance with the invention is disclosed by DE-C 2830765. However, the two-zone tube bundle reactors disclosed in DE-C 2513405, U.S. Pat. No. 3,147,084, DE-A 2201528, EP-A 383224 and DE-A 2903582 are also suitable.

In other words, in the simplest manner, the fixed catalyst bed to be used in accordance with the invention is disposed in the uniformly charged metal tubes of a tube bundle reactor and two substantially spatially separated heating media, generally salt melts, are conducted around the metal tubes. The tube section over which the particular salt bath extends represents a temperature or reaction zone.

For example, a salt bath A preferably flows around that section of the tubes (the reaction zone A) in which the oxidative conversion of propene (in single pass) proceeds until a conversion value in the range from 40 to 80 mol. % is achieved and a salt bath B preferably flows around the section of the tubes (reaction zone B) in which the subsequent oxidative conversion of propene (in single pass) proceeds until a conversion value of generally at least 90 mol % is achieved (if required, reaction zones A, B may be followed by further reaction zones which are kept at individual temperatures).

Within the particular temperature zone, the salt bath may in principle be conducted as in the one-zone method. The inlet temperature of the salt bath B is normally from at least 5 to 10° C. above the temperature of the salt bath A. Otherwise, the inlet temperatures may be within the temperature range for the inlet temperature recommended for the one-zone method.

Otherwise, the two-zone high-load method may be carried out as described, for example, in DE-A 10308836, EP-A 1106598 or as described in WO 01/36364, or DE-A 19927624, or DE-A 19948523, DE-A 10313210, DE-A 10313213 or as described in DE-A 19948248.

Accordingly, the process according to the invention is suitable for propene hourly space velocities on the fixed catalyst bed of $\geq 70$ l (STP)/l·h, $\geq 90$ l (STP)/l·h, $\geq 110$ l (STP)/l·h, $\geq 130$ l (STP)/l·h, $\geq 140$ l (STP)/l·h, $\geq 160$ l (STP)/l·h, $\geq 180$ l (STP)/l·h, $\geq 240$ l (STP)/l·h, $\geq 300$ l (STP)/l·h, but normally $\geq 600$ l (STP)/l·h. Here (i.e. generally in the case of propene hourly space velocities in this document), in a departure from the norm in this document, the hourly space velocity is based on the volume of the fixed catalyst bed excluding any sections used which consist exclusively of inert material.

The inert gas to be used for the charge gas mixture may consist, for example, of $\geq 20\%$ by volume, or $\geq 30\%$ by volume, or $\geq 40\%$ by volume, or $\geq 50\%$ by volume, or $\geq 60\%$ by volume, or $\geq 70\%$ by volume, or $\geq 80\%$ by volume, or $\geq 90\%$ by volume, or $\geq 95\%$ by volume, of molecular nitrogen.

The inert diluent gas may also consist, for example, of from 2 to 35 or 20% by weight of $H_2O$ and from 65 to 98% by volume of $N_2$.

However, at propene hourly space velocities on the fixed catalyst bed of above 250 l (STP)/l·h, the use is recommended for the process according to the invention of inert diluent gases such as propane, ethane, methane, butane, pentane, $CO_2$, CO, steam and/or noble gases. However, it will be appreciated that these gases may also be used at lower propene hourly space velocities.

The working pressure in the course of the inventive gas phase partial oxidation of the propene may be either below atmospheric pressure (for example up to 0.5 bar) or above atmospheric pressure. Typically, the working pressure in the gas phase partial oxidation of propene will be at values of from 1 to 5 bar, frequently from 1 to 3 bar.

Normally, the reaction pressure in the inventive propene partial oxidation will not exceed 100 bar.

The molar $O_2$:propene ratio in the starting reaction gas mixture which is conducted through the fixed catalyst bed in the process according to the invention will normally be $\geq 1$. Typically, this ratio will be at values of $\leq 3$. According to the invention, the molar $O_2$:propene ratio in the aforementioned charge gas mixture will frequently be from 1:2 to 1:1.5. In many cases, the process according to the invention will be performed at a propene:oxygen:inert gas (including steam) volume ratio (l(STP)) in the starting reaction gas mixture of 1:(1 to 3):(3 to 30), preferably of 1:(1.5 to 2.3):(10 to 15

The propene fraction in the starting reaction gas mixture may lie, for example, at values of from 4 or 7 to 20% by volume, frequently from 5 or 7 to 15% by volume or from 5 or 7 to 12% by volume or from 5 to 8% by volume (based in each case on the total volume).

A typical composition of the starting reaction gas mixture (irrespective of the hourly space velocity selected) may contain, for example, the following components:
から 6 to 6.5% by volume of propene,
from 3 to 3.5% by volume of $H_2O$,
from 0.3 to 0.5% by volume of CO,
from 0.8 to 1.2% by volume of $CO_2$,
from 0.025 to 0.04% by volume of acrolein,
from 10.4 to 10.7% by volume of $O_2$ and,
as the remainder ad 100%, molecular nitrogen, or:
5.4% by volume of propene,
10.5% by volume of oxygen,
1.2% by volume of $CO_x$,
81.3% by volume of $N_2$ and
1.6% by volume of $H_2O$.

However, the starting reaction gas mixture may also have the following composition:
from 6 to 15% by volume of propene,
from 4 to 30% by volume (frequently from 6 to 15% by volume) of water,
from $\geq 0$ to 10% by volume (preferably from $\geq 0$ to 5% by volume) of constituents other than propene, water, oxygen and nitrogen, sufficient molecular oxygen that the molar ratio of molecular oxygen present to molecular propene present is from 1.5 to 2.5, and, as the remainder up to 100% by volume of the total amount, molecular nitrogen.

Another possible starting reaction gas mixture composition may contain:
6.0% by volume of propene,
60% by volume of air and
34% by volume of $H_2O$.

Alternatively, starting reaction gas mixtures of the composition according to Example 1 of EP-A 990 636, or according to Example 2 of EP-A 990 636, or according to Example 3 of EP-A 1 106 598, or according to Example 26 of EP-A 1 106 598, or according to Example 53 of EP-A 1 106 598, may also be used.

Further starting reaction gas mixtures which are suitable in accordance with the invention may lie within the following composition framework:
from 7 to 11% by volume of propene,
from 6 to 12% by volume of water,
from $\geq 0$ to 5% by volume of constituents other than propene, water, oxygen and nitrogen,
sufficient molecular oxygen that the molar ratio of oxygen present to molecular propene present is from 1.4 to 2.2, and,
as the remainder up to 100% by volume of the total amount, molecular nitrogen.

The propene to be used in the starting reaction gas mixture is in particular polymer-grade propene and chemical-grade propene, as described, for example, by DE-A 10232748.

The oxygen source used is normally air.

To prepare the fixed catalyst bed, it is possible to use in the process according to the invention only the appropriate shaped catalyst bodies having multimetal oxide active composition or else substantially homogeneous mixtures of shaped catalyst bodies having multimetal oxide active composition and shaped bodies having no multimetal oxide active composition which behave substantially inertly with respect to the heterogeneously catalyzed partial gas phase oxidation (and consist of inert material) (shaped diluent bodies). Useful materials for such inert shaped bodies are in principle all of those which are also suitable as support materials for coated catalysts which are suitable in accordance with the invention. Useful such materials are, for example, porous or nonporous aluminum oxides, silicon dioxide, thorium dioxide, zirconium dioxide, silicon carbide, silicates such as magnesium or aluminum silicate or the steatite already mentioned (for example Steatite C-220 from CeramTec).

The geometry of such inert shaped diluent bodies may in principle be as desired. In other words, they may be, for example, spheres, polygons, solid cylinders or else rings. According to the invention, the inert shaped diluent bodies selected will preferably be those whose geometry corresponds to that of the shaped catalyst bodies to be diluted by them.

In general, it is favorable when the chemical composition of the active composition used does not change over the fixed catalyst bed. In other words, although the active composition used for an individual shaped catalyst body may be a mixture of different multimetal oxides comprising the elements Mo and/or W and also at least one of the elements Bi, Fe, Sb, Sn and Cu, the same mixture then advantageously has to be used for all shaped catalyst bodies of the fixed catalyst bed.

The volume-specific (i.e. normalized to the unit of the volume) activity preferably normally increases continuously, abruptly or in stages within the fixed catalyst bed in the flow direction of the starting reaction gas mixture.

The volume-specific activity may, for example, be reduced in a simple manner by homogeneously diluting a basic amount of shaped catalyst bodies prepared in a uniform manner with shaped diluent bodies. The higher the fraction of the shaped diluent bodies selected, the lower the amount of active composition, i.e. catalyst activity, in a certain volume of the fixed bed.

A volume-specific activity increasing at least once in the flow direction of the reaction gas mixture over the fixed catalyst bed can thus be attained in a simple manner for the process according to the invention, for example, by beginning the bed with a high fraction of inert shaped diluent bodies based on one type of shaped catalyst bodies, and then reducing this fraction of shaped diluent bodies in the flow direction either continuously or, once or more than once, abruptly (for example in stages). However, an increase in the volume-specific activity is also possible, for example, by, at constant geometry and active composition type of a shaped coated catalyst body, increasing the thickness of the active composition layer applied to the support, or, in a mixture of coated catalysts having the same geometry but having different proportions by weight of the active composition, increasing the fraction of shaped catalyst bodies having a higher proportion by weight of active composition. Alternatively, the active compositions themselves may also be diluted by, in the course of active composition preparation, for example, incorporating inert diluting materials such as hard-fired silicon dioxide into the dry mixture of starting compounds to be calcined. Different addition amounts of diluting material automatically lead to different activities. The more diluting material is added, the lower the resulting activity will be. A similar effect can also be achieved, for example, by appropriately varying the mixing ratio in mixtures of unsupported catalysts and of coated catalysts (with identical active composition). It will be appreciated that the variants described may also be employed in combination.

Of course, mixtures of catalysts having chemically different active compositions and, as a consequence of this different composition, different activity may also be used for the fixed catalyst bed. These mixtures may in turn be diluted with inert diluent bodies.

Upstream and/or downstream of the sections of the fixed catalyst bed having active composition may be disposed beds consisting exclusively of inert material (for example only shaped diluent bodies) (in this document, they are included for terminology purposes in the fixed catalyst bed, unless stated otherwise). These may likewise be brought to the temperature of the fixed catalyst bed. The shaped diluent bodies used for the inert bed may have the same geometry as the shaped catalyst bodies used for the sections of the fixed catalyst bed having active composition. However, the geometry of the shaped diluent bodies used for the inert bed may also be different to the aforementioned geometry of the shaped catalyst bodies (for example, spherical instead of annular).

Frequently, the shaped bodies used for such inert beds have the annular geometry 7 mm×7 mm×4 mm (external diameter×length×internal diameter) or the spherical geometry having the diameter d=4–5 mm.

In many cases, the section having active composition of the fixed catalyst bed is structured as follows in the flow direction of the reaction gas mixture in the process according to the invention.

First, to a length of from 10 to 60%, preferably from 10 to 50%, more preferably from 20 to 40% and most preferably from 25 to 35% (i.e., for example, to a length of from 0.70 to 1.50 m, preferably from 0.90 to 1.20 m), each of the total length of the section of the fixed catalyst bed charge having active composition, one homogeneous mixture or two successive homogeneous mixtures (having decreasing dilution) of shaped catalyst bodies and shaped diluent bodies (both preferably having substantially the same geometry), in which the proportion by weight of shaped diluent bodies (the mass densities of shaped catalyst bodies and of shaped diluent bodies generally differ only slightly) is normally from 5 to 40% by weight, preferably from 10 to 40% by weight or from 20 to 40% by weight and more preferably from 25 to 35% by weight. Downstream of this first zone is then-frequently advantageously disposed, up to the end of the length of the section of the fixed catalyst bed having active composition (i.e., for example, to a length of from 2.00 to 3.00 m, preferably from 2.50 to 3.00 m), either a bed of shaped catalyst bodies which is diluted only to a lesser extent (than in the first zone), or, most preferably, a sole bed of the same shaped catalyst bodies which have also been used in the first zone.

The aforementioned is especially true when the shaped catalyst bodies used in the fixed catalyst bed are unsupported catalyst rings or coated catalyst rings (especially those which are listed in this document as preferred). For the purposes of the aforementioned structuring, both the shaped catalyst bodies or their support rings and the shaped diluent bodies in the process according to the invention advantageously have substantially the ring geometry 5 mm×3 mm×2 mm (external diameter×length×internal diameter).

The aforementioned is also true when, instead of inert shaped diluent bodies, shaped coated catalyst bodies are used whose active composition content is from 2 to 15% by weight lower than the active composition content of the shaped coated catalyst bodies at the end of the fixed catalyst bed.

A pure inert material bed whose length, based on the total length of the fixed catalyst bed, is appropriately from 1 or 5 to 20% generally begins the fixed catalyst bed in the flow direction of the reaction gas mixture. It is normally used as a heating zone for the reaction gas mixture.

Typically, the catalyst tubes in the tube bundle reactors are manufactured from ferritic steel and typically have a wall thickness of from 1 to 3 mm. Their internal diameter is generally (uniformly) from 20 to 30 mm, frequently from 21 to 26 mm. Appropriately from an application point of view, the number of catalyst tubes accommodated in the tube bundle reactor is at least 5 000, preferably at least 10 000. Frequently, the number of catalyst tubes accommodated in the reaction vessel is from 15 000 to 30 000. Tube bundle reactors having a number of catalyst tubes above 40 000 are usually exceptional. Within the vessel, the catalyst tubes are normally arranged in homogeneous distribution, and the distribution is appropriately selected in such a way that the separation of the central internal axes of immediately adjacent catalyst tubes (known as the catalyst tube pitch) is from 35 to 45 mm (cf., for example, EP-B 468290).

The hourly space velocity on the fixed catalyst bed (here excluding pure inert sections) of reaction gas mixture in the process according to the invention will typically be from 1 000 to 10 000 l (STP)/l·h, usually from 1 000 to 5 000 l (STP)/l·h, frequently from 1 500 to 4 000 l (STP)/l·h.

When the process according to the invention is performed, a fresh fixed catalyst bed, after it has been conditioned, will normally be operated in such a way that, after determining the composition of the starting reaction gas mixture and determining the hourly space velocity on the fixed catalyst bed of starting reaction gas mixture, the temperature of the fixed catalyst bed (or the inlet temperature of the heating medium into the heating zone of the tube bundle reactor) is adjusted in such a way that the conversion $C^{pro}$ of propene on single pass of the reaction gas mixture through the fixed catalyst bed is at least 90 mol %. When favorable catalysts are used, values of $C^{pro}$ of $\geq 92$ mol %, or $\geq 93$ mol % or $\geq 94$ mol %, or $\geq 96$ mol % and frequently even more are also possible.

When the heterogeneously catalyzed partial oxidation of propene to acrolein and in some cases also acrylic acid is performed continuously, the composition of the starting reaction gas mixture and the hourly space velocity on the fixed catalyst bed of starting reaction gas mixture will be kept substantially constant (if desired, the hourly space velocity is adapted to the fluctuating market demand). A fall in the activity of the fixed catalyst bed over the time will normally be counteracted under these production conditions by increasing the temperature of the fixed catalyst bed (the inlet temperature of the heating medium into the temperature zone of the tube bundle reactor) from time to time (the flow rate of the heating medium is normally likewise kept substantially constant), in order to keep the propene conversion on single pass of the reaction gas mixture within the desired target corridor (i.e. at $C^{pro}$ of $\geq 90$ mol % or $\geq 92$ mol %, or $\geq 93$ mol %, or $\geq 94$ mol % or $\geq 96$ mol %). However, such a procedure is accompanied by the disadvantages described at the outset of this document.

According to the invention, the procedure will therefore advantageously be to interrupt the gas phase partial oxidation at least once per calendar year, in order to conduct a gas mixture G consisting of molecular oxygen, inert gas and optionally steam through the fixed catalyst bed at a temperature of the fixed catalyst bed of from 250 to 550° C. Subsequently, the partial oxidation is continued while substantially retaining the process conditions (preference is given to restoring the propene hourly space velocity slowly to its value as described, for example, in DE-A 10337788) and the temperature of the fixed catalyst bed is adjusted in such a way that the propene conversion attains the desired target value. In general, this temperature value, for the same conversion, will be at a somewhat lower value than the temperature that the fixed catalyst bed had before the interruption of the partial oxidation and the inventive treatment with the gas mixture G. Starting from this temperature value of the fixed catalyst bed, the partial oxidation is continued while substantially retaining the remaining conditions, and the fall in the activity of the fixed catalyst bed over the time will appropriately in turn be counteracted by increasing the temperature of the fixed catalyst bed from time to time. Within one calendar year, the partial oxidation, in accordance with the invention, is in turn interrupted at least once, in order to conduct the gas mixture G through the fixed catalyst bed in the inventive manner. Afterward, the partial oxidation, advantageously in accordance with the invention, is started up again as described, etc.

It is surprising that in the long-term operation of a heterogeneously catalyzed gas phase partial oxidation of propene to acrolein and in some cases acrylic acid, the intensity of the hotspot expansion in the process according to the invention has more favorable behavior than in prior art processes. The process according to the invention thus enables on the one hand longer on-stream times of a fixed catalyst bed in a reactor before it has to be partly or fully exchanged. On the other hand, the propene conversion achieved, integrated over time, is also increased and the selectivity of target product formation is likewise promoted. One factor which contributes to this is that the location of the hotspot in the process according to the invention remains stationary or normally migrates over time in the direction of the inlet point of the reaction gas mixture into the fixed catalyst bed. The hotspot thus migrates in the reaction gas mixture increasingly into the region in which the acrolein content is still not very pronounced. This reduces the possibility that acrolein which has already formed undergoes partial undesired full combustion under the influence of the hotspot temperature. The hotspot temperature can be determined in the process according to the invention in tube bundle reactors, for example, by means of thermal tubes, as described in EP-A 873 783, WO 03-076373 and in EP-A 1 270 065. The number of such thermal tubes within a tube bundle reactor is appropriately from 4 to 20. Advantageously, they are arranged in uniform distribution within the tube bundle interior.

Frequently, the increase in the fixed catalyst bed temperature in the process according to the invention will be carried out in such a way that the propene conversion on single pass of the reaction mixture through the catalyst bed does not go below 90 mol %, or 92 mol %, or 93 mol %, or 94 mol %, or 96 mol % or 97 mol %. In other words, the fixed catalyst bed temperature will normally be increased at least once before 7500 or before 7000, usually before 6000 and in many cases before 5000 or 4000, operating hours of the partial oxidation have been attained.

Finally, it should be emphasized that the increase in the fixed catalyst bed temperature over the time in the process according to the invention employing particularly favorable catalysts (for example those recommended in this document) is preferably carried out (usually substantially continuously and) in such a way that the propene content in the product gas mixture does not exceed the value of 10 000 ppm by weight, preferably 6000 ppm by weight and more preferably 4000 or 2000 ppm by weight. In addition, the residual oxygen in the product gas mixture should generally be at least 1% by volume, preferably at least 2% by volume and more preferably at least 3% by volume.

The process according to the invention is especially advantageous when it is operated at a propene hourly space velocity on the fixed catalyst bed of $\geq 120$ l (STP)/l·h, or $\geq 130$ l (STP)/l·h, or $\geq 140$ l (STP)/l·h. Finally, it should be emphasized that the process according to the invention is suitable in a corresponding manner for the long-term operation of a heterogeneously catalyzed gas phase partial oxidation of isobutene, the methyl ether of tert-butanol and/or of tert-butanol to methacrolein (especially when the same catalyst systems are employed; however, the process conditions and catalyst systems of WO 03/039744 are also useful). Generally, the freshly charged catalyst bed will be configured in such a way that, as described in EP-A 990636 and EP-A 1106598, both the hotspot development and its temperature sensitivity are very low. Furthermore, both in the case of first start up and in the case of restart after the process according to the invention has been performed, the hourly space velocity on the fixed catalyst bed of propene will advantageously be left at values of $\leq 100$ l (STP)/l·h until steady-state operation has been established.

EXAMPLES

A) Preparation of the Catalyst Used

Preparation of an annular unsupported catalyst having the following stoichiometry of the active multimetal oxide II:

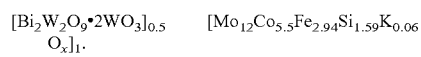

1. Preparation of a Starting Composition 1

209.3 kg of tungstic acid (72.94% by weight of W) were stirred in portions into 775 kg of an aqueous bismuth nitrate solution in nitric acid (11.2% by weight of Bi; free nitric acid from 3 to 5% by weight; mass density: 1.22 to 1.27 g/ml) at 25° C. The resulting aqueous mixture was subsequently stirred at 25° C. for a further 2 h and subsequently spray-dried.

The spray-drying was effected in a rotating disc spray tower in countercurrent at a gas inlet temperature of 300±10° C. and a gas outlet temperature of 100±10° C. The resulting spray powder (particle size a substantially uniform 30 μm) which had an ignition loss of 12% by weight (ignite at 600° C. under air for 3 h) was subsequently converted to a paste in a kneader using 16.8% by weight (based on the powder) of water and extruded by means of an extruder (rotational moment: $\leq 50$ Nm) to extrudates of diameter 6 mm. These were cut into sections of 6 cm, dried under air on a 3-zone belt dryer at a residence time of 120 min at temperatures of 90–95° C. (zone 1), 125° C. (zone 2) and 125° C. (zone 3), and then thermally treated at a temperature in the range from 780 to 810° C. (calcined; in a rotary tube oven flowed through by air (capacity 1.54 m³, 200 m³ (STP) of air/h)). When precisely adjusting the calcination temperature, it is essential that it is directed to the desired phase composition of the calcination product. The desired phases are WO₃ (monoclinic) and Bi₂W₂O₉; the presence of γ-Bi₂WO₆ (Russellite) is undesired. Therefore, should the compound γ-Bi₂WO₆ still be detectable by a reflection in the x-ray powder diffractogram at a reflection angle of 2θ=28.4° (CuKa radiation) after the calcination, the preparation has to be repeated and the calcination temperature increased within the temperature range specified or the residence time increased at constant calcination temperature, until the disappearance of the reflection is achieved. The preformed calcined mixed oxide obtained in this way was ground so that the $X_{50}$ value (cf. Ullmann's Encyclopedia of Industrial Chemistry, 6th Edition (1998) Electronic Release, Chapter 3.1.4 or DIN 66141) of the resulting particle size was 5 mm. The ground material was then mixed with 1% by weight (based on the ground material) of finely divided $SiO_2$ from Degussa of the Sipernat® type (bulk density 150 g/l; $X_{50}$ value of the $SiO_2$ particles was 10 µm, the BET surface area was 100 m²/g).

2. Preparation of a Starting Composition 2

A solution A was prepared by dissolving 213 kg of ammonium heptamolybdate tetrahydrate (81.5% by weight of $MoO_3$) at 60° C. with stirring in 600 l of water and the resulting solution was admixed while maintaining the 60° C. and stirring with 0.97 kg of an aqueous potassium hydroxide solution (46.8% by weight of KOH) at 20° C.

A solution B was prepared by introducing 116.25 kg of an aqueous iron(III) nitrate solution (14.2% by weight of Fe) at 60° C. into 262.9 kg of an aqueous cobalt(II) nitrate solution (12.4% by weight of Co). Subsequently, while maintaining the 60° C., solution B was continuously pumped into the initially charged solution A over a period of 30 minutes. Subsequently, the mixture was stirred at 60° C. for 15 minutes. 19.16 kg of a Ludox silica gel from Dupont (46.80% by weight of $SiO_2$, density: from 1.36 to 1.42 g/ml, pH from 8.5 to 9.5, max. alkali content 0.5% by weight) were then added to the resulting aqueous mixture, and the mixture was stirred afterward at 60° C. for a further 15 minutes.

Subsequently, the mixture was spray-dried in countercurrent in a rotating disc spray tower (gas inlet temperature: 400±10° C., gas outlet temperature: 140±5° C.). The resulting spray powder had an ignition loss of approx. 30% by weight (ignite under air at 600° C. for 3 h) and a substantially uniform particle size of 30 µm.

3. Preparation of the Multimetal Oxide Active Composition II

The starting composition 1 was mixed homogeneously with the starting composition 2 in the amounts required for a multimetal oxide active composition of the stoichiometry

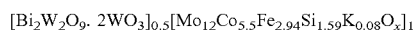

$[Bi_2W_2O_9 \cdot 2WO_3]_{0.5}[Mo_{12}Co_{5.5}Fe_{2.94}Si_{1.59}K_{0.08}O_x]_1$ in a mixer having bladed heads. Based on the aforementioned overall composition, an additional 1% by weight of finely divided graphite from Timcal AG (San Antonio, US) of the TIMREX P44 type (sieve analysis: min. 50% by weight <24 mm, max. 10% by weight $\geq$24 µm and $\leq$48 µm, max. 5% by weight >48 µm, BET surface area: from 6 to 13 m²/g) were mixed in homogeneously. The resulting mixture was then conveyed in a compactor (from Hosokawa Bepex GmbH, D-74211 Leingarten) of the K200/100 compactor type having concave, fluted smooth rolls (gap width: 2.8 mm, sieve width: 1.0 mm, lower particle size sieve width: 400 µm, target compressive force: 60 kN, screw rotation rate: from 65 to 70 revolutions per minute). The resulting compactate had a hardness of 10 N and a substantially uniform particle size of from 400 µm to 1 mm.

The compactate was subsequently mixed with, based on its weight, a further 2% by weight of the same graphite and subsequently compressed in a Kilian rotary tableting press of the Rx73 type from Kilian, D-50735 Cologne, under a nitrogen atmosphere to give annular shaped unsupported catalyst precursor bodies of the geometry (external diameter×length×internal diameter) 5 mm×3 mm×2 mm having a side crushing strength of 19 N±3 N.

In this document, side crushing strength refers to the crushing strength when the annular shaped unsupported catalyst precursor body is compressed at right angles to the cylinder surface (i.e. parallel to the surface of the ring orifice).

All side crushing strengths in this document relate to a determination by means of a material testing machine from Zwick GmbH & Co. (D-89079 Ulm) of the Z 2.5/TS1S type. This material testing machine is designed for quasistatic stress having an single-impetus, stationary, dynamic or varying profile. It is suitable for tensile, compressive and bending tests. The installed force transducer of the KAF-TC type from A.S.T. (D-01307 Dresden) having the manufacturer number 03-2038 was calibrated in accordance with DIN EN ISO 7500-1 and could be used for the 1–500 N measurement range (relative measurement uncertainty: ±0.2%).

The measurements were carried out with the following parameters:
Initial force: 0.5 N.
Rate of initial force: 10 mm/min.
Testing rate: 1.6 mm/min.

The upper die was initially lowered slowly down to just above the cylinder surface of the annular shaped unsupported catalyst precursor body. The upper die was then stopped, in order subsequently to be lowered at the distinctly slower testing rate with the minimum initial force required for further lowering.

The initial force at which the shaped unsupported catalyst precursor body exhibits crack formation is the side crushing strength (SCS).

For the final thermal treatment, in each case 1000 g of the shaped unsupported catalyst precursor bodies were heated in a muffle furnace flowed through by air (capacity 60 l, 1 l/h of air per gram of shaped unsupported catalyst precursor body) from room temperature (25° C.) to 190° C. initially at a heating rate of 180° C./h. This temperature was maintained for 1 h and then increased to 210° C. at a heating rate of 60° C./h. The temperature of 210° C. was in turn maintained over 1 h before it was increased to 230° C. at a heating rate of 60° C./h. This temperature was likewise maintained for 1 h before it was increased to 265° C., again at a heating rate of 60° C./h. The temperature of 265° C. was subsequently likewise maintained over 1 h. Afterward, the furnace was initially cooled to room temperature and the decomposition phase thus substantially completed. The furnace was then heated to 465° C. at a heating rate of 180° C./h and this calcination temperature maintained over 4 h.

Annular unsupported catalysts were obtained from the annular shaped unsupported catalyst precursor bodies.

The specific surface area S, the total pore volume V, the pore diameter $d^{max}$ which makes the greatest contribution to the total pore volume, and the percentages of those pore diameters whose diameter is >0.1 and $\leq$1 µm in the total pore volume for the resulting annular unsupported catalysts were as follows:
S=7.6 m²/g.
V=0.27 cm³/g.
$d^{max}$ [µm]=0.6.
$V^{0.1}_1$-%=79.

In addition, the ratio R of apparent mass density to true mass density ρ (as defined in EP-A 1340538) was 0.66.

On the industrial scale, the same annular catalyst was prepared by thermal treatment using a belt calcining apparatus as described in Example 1 of DE-A 10046957 (except that the bed height in the decomposition (chambers 1 to 4) was advantageously 44 mm at a residence time per chamber of 1.46 h and, in the calcination (chambers 5 to 8), it was advantageously 130 mm at a residence time of 4.67 h); the chambers had a surface area (at a uniform chamber length of 1.40 m) of 1.29 m² (decomposition) and 1.40 m² (calcination) and were flowed through from below through the coarse-mesh belt by 75 m³ (STP)/h of supply air which was aspirated by means of rotating ventilators. Within the chambers, the temporal and local deviation of the temperature from the target value was always ≦2° C. Otherwise, the procedure was as described in Example 1 of DE-A 10046957.

B) Performance of the Partial Oxidation

I. Description of the General Process Conditions

| | |
|---|---|
| Heat exchange medium used: | salt melt consisting of 60% by weight of potassium nitrate and 40% by weight of sodium nitrite. |
| Material of the catalyst tubes: | ferritic steel. |
| Dimensions of the catalyst tubes: | length 3200 mm; internal diameter 25 mm; external diameter 30 mm (wall thickness: 2.5 mm). |

Number of catalyst tubes in the tube bundle: 25 500.
Reactor: Cylindrical vessel of diameter 6 800 mm; annularly arranged tube bundle having a free central space.
 Diameter of the central free space: 1 000 mm. Distance of the outermost catalyst tubes from the vessel wall: 150 mm. Homogeneous catalyst tube distribution in the tube bundle (6 equidistant neighboring tubes per catalyst tube).
 Catalyst tube pitch: 38 mm.
 The catalyst tubes were secured and sealed by their ends in catalyst tube plates of thickness 125 mm and opened with their orifices each into a hood connected to the vessel at the upper or lower end.
 Feed of the heat exchange medium to the tube bundle:
 The tube bundle was divided by three deflecting plates (thickness in each case 10 mm) mounted in succession between the catalyst tube plates in the longitudinal direction into 4 equidistant (each 730 mm) longitudinal sections (zones).
 The uppermost and the lowermost deflecting plate had annular geometry, the internal annular diameter was 1000 mm and the external annular diameter extended with sealing to the vessel wall. The catalyst tubes were not secured and sealed to the deflecting plates. Rather, a gap having a gap width of <0.5 mm was left in such a way that the transverse flow rate of the salt melt was substantially constant within one zone.
 The middle deflecting plate was circular and extended up to the outermost catalyst tubes of the tube bundle.
 The recycling of the salt melt was brought about by two salt pumps, each of which supplied one longitudinal half of the tube bundle.
 The pumps compressed the salt melt into an annular channel which was arranged at the bottom around the reactor jacket and divided the salt melt over the vessel circumference. The salt melt reached the tube bundle in the lowermost longitudinal section through windows in the reactor jacket. The salt melt then flowed as dictated by the deflecting plates in the sequence
  from the outside inward,
  from the inside outward,
  from the outside inward,
  from the inside outward, in a substantially meandering manner, viewed over the vessel, from bottom to top. The salt melt collected through windows mounted in the uppermost longitudinal section around the vessel circumference in an annular channel mounted at the top around the reactor jacket and, after cooling to the original inlet temperature, was compressed back into the lower annular channel by the pumps.
 The composition of the starting reaction gas mixture (mixture of air, chemical-grade propylene and cycle gas) over the operating time was within the following framework:
 from 5 to 7% by volume of chemical-grade propene,
 from 10 to 14% by volume of oxygen,
 from 1 to 2% by volume of $CO_x$,
 from 1 to 3% by volume of $H_2O$, and
 at least 80% by volume of $N_2$.

| | |
|---|---|
| Reactor charge: | Salt melt and reaction gas mixture were conducted in countercurrent viewed over the reactor. The salt melt entered at the bottom, the reaction gas mixture at the top.<br>The inlet temperature of the salt melt was 337° C. at the start (on completion of conditioning of the fixed catalyst bed).<br>The associated outlet temperature of the salt melt at the start was 339° C.<br>The pump output was 6200 m³ of salt melt/h.<br>The starting reaction gas mixture was fed to the reactor at a temperature of 300° C. |
| Propene loading of the fixed catalyst bed: | from 90 to 120 l (STP)/l · h |
| Catalyst tube charge with fixed catalyst bed (from top to bottom): | Zone A: 50 cm<br>Preliminary bed of steatite rings of geometry 7 mm × 7 mm × 4 mm (external diameter × length × internal diameter)<br>Zone B: 100 cm<br>catalyst charge with a homogeneous mixture of 30% by weight of steatite rings of geometry 5 mm × 3 mm × 2 mm (external diameter × length × internal diameter) and 70% by weight of the annular unsupported catalyst prepared.<br>Zone C: 170 cm<br>catalyst charge with the annular (5 mm × 3 mm × 2 mm = external diameter × length × internal diameter) unsupported catalyst prepared. |

The thermal tubes (their number was 10 which were uniformly distributed in the central region of the tube bundle) were configured and charged as follows: (they were used to determine the hotspot temperature; this is an arithmetic average of independent measurements in the 10 thermal tubes)
 Each of the 10 thermal tubes had a central thermowell having 40 temperature measurement points (i.e. each thermal tube contained 40 thermoelements which were integrated into a thermowell at different lengths and thus formed a multithermoelement by which the temperature could be simultaneously determined within the thermal tube at different heights).
 At least 13 and at most 30 of the in each case 40 temperature measurement points were in the region of the first meter of the active section of the fixed catalyst bed (in the flow direction of the reaction gas mixture).
 The internal diameter of a thermal tube was 27 mm. The wall thickness and tube material were as in the working tubes.
 The external diameter of the thermowell was 4 mm.
 A thermal tube was charged with the annular unsupported catalyst prepared. In addition, catalyst spall which had been generated from the annular unsupported catalyst and had a longest dimension of from 0.5 to 5 mm was charged into the thermal tube.

The catalyst spall was charged in homogeneous distribution over the entire active section of the fixed catalyst bed of the particular thermal tube in such a way that the pressure drop of the reaction gas mixture as it passed through the thermal tube corresponded to that as the reaction gas mixture passed through a working tube (for this purpose, from 5 to 20% by weight of catalyst spall were required based on the active section of the fixed catalyst bed (i.e. excluding the inert sections) in the thermal tube). At the same time, the particular total fill height of active and inert sections in the working and thermal tubes was the same and the ratio of the total amount of active composition present in the tube to heat exchange surface area of the tube in working and thermal tubes was set at substantially the same value.

II. Long-Term Operation (Results)

The target conversion for the propene to be converted in single pass of the reaction gas mixture through the fixed catalyst bed was set at 97.5 mol %.

Successive increases in the inlet temperature of the salt melt allowed this conversion value to be maintained over the time when the process was carried out continuously.

Once per calendar month the partial oxidation was interrupted, the inlet temperature of the salt melt which was last employed was retained and a gas mixture G composed of 6% by volume of $O_2$ and 95% by volume of $N_2$ was conducted through the fixed catalyst bed at an hourly space velocity on the fixed catalyst bed of 30 l (STP)/l•h for a period $t_G$ of from 24 h to 48 h.

The inlet temperature of the salt melt and the hotspot temperature and also the selectivity $S^{AC+AA}$ of acrolein formation and acrylic acid by-production developed as follows (the temperature data (apart from the start) relate in all cases to the time in each case which was just before the interruption of the partial oxidation and the treatment of the fixed catalyst bed with the gas mixture G):

| | |
|---|---|
| Start: | Salt melt inlet temperature = 318° C. |
| | Hotspot temperature = 368° C. |
| | $S^{AC+AA}$ = 94.6 mol % |
| after 1 year of operating time: | Salt melt inlet temperature = 322° C. |
| | Hotspot temperature = 371° C. |
| | $S^{AC+AA}$ = 94.8 mol % |
| after 2 years of operating time: | Salt melt inlet temperature = 326° C. |
| | Hotspot temperature = 373° C. |
| | $S^{AC+AA}$ = 95.0 mol % |
| after 3 years of operating time: | Salt melt inlet temperature = 332° C. |
| | Hotspot temperature = 377° C. |
| | $S^{AC+AA}$ = 95.4 mol % |
| after 4 years of operating time: | Salt melt inlet temperature = 339° C. |
| | Hotspot temperature = 379° C. |
| | $S^{AC+AA}$ = 95.6 mol % |
| after 5 years of operating time: | Salt melt inlet temperature = 345° C. |
| | Hotspot temperature = 385° C. |
| | $S^{AC+AA}$ = 95.6 mol % |

U.S. provisional patent application No. 60/515,114, filed on Oct. 29, 2003, is incorporated into the present application by literature reference.

With reference to the abovementioned teachings, numerous alterations and deviations from the present invention are possible. It may therefore be assumed that the invention, within the scope of the appended claims, may be performed differently from the way specifically described herein.

We claim:

1. A process for the long-term operation of a heterogeneously catalyzed gas phase partial oxidation of propene to acrolein, by:
    conducting a starting reaction gas mixture which comprises propene, molecular oxygen and at least one inert diluent gas through a fixed catalyst bed at elevated temperature whose catalysts are such that their active composition is at least one multimetal oxide which contains the elements molybdenum and/or tungsten and also at least one of the elements bismuth, tellurium, antimony, tin and copper, and by, in order to counteract the deactivation of the fixed catalyst bed, and
    increasing the temperature of the fixed catalyst bed over the time, which comprises interrupting the gas phase partial oxidation at least once per calendar year and conducting a gas mixture G consisting of molecular oxygen, inert gas and optionally steam through the fixed catalyst bed at a temperature of the fixed catalyst bed of from 250 to 550° C.

2. A process as claimed in claim 1, wherein the gas phase partial oxidation is interrupted at least once per calendar quarter and a gas mixture G consisting of molecular oxygen, inert gas and optionally steam is conducted through the fixed catalyst bed at a temperature of the fixed catalyst bed of from 250 to 550° C.

3. A process as claimed in claim 1, wherein the gas phase partial oxidation is interrupted at least once per calendar month and a gas mixture G consisting of molecular oxygen, inert gas and optionally steam is conducted through the fixed catalyst bed at a temperature of the fixed catalyst bed of from 250 to 550° C.

4. A process as claimed in claim 1, wherein the period over which the gas mixture G is conducted through the fixed catalyst bed is from 2 h to 120 h.

5. A process as claimed in claim 1, wherein the gas mixture G which is conducted through the fixed catalyst bed contains at least 4% by volume of oxygen.

6. A process as claimed in claim 1, which is carried out in a tube bundle reactor.

7. A process as claimed in claim 1, wherein the active composition of the catalysts is a multimetal oxide containing Mo, Bi and Fe.

8. A process as claimed in claim 1, wherein the active composition of the catalysts is at least one multimetal oxide of formula I

$$Mo_{12}Bi_aFe_bX^1_cX^2_dX^3_eX^4_fO_n \qquad (I)$$

in which the variables are each defined as follows:
    $X^1$=nickel and/or cobalt,
    $X^2$=thallium, an alkali metal and/or an alkaline earth metal,
    $X^3$=zinc, phosphorus, arsenic, boron, antimony, tin, cerium, lead and/or tungsten,
    $X^4$=silicon, aluminum, titanium and/or zirconium,
    a=from 0.5 to 5,
    b=from 0.01 to 5, preferably from 2 to 4,
    c=from 0 to 10, preferably from 3 to 10,
    d=from 0 to 2, preferably from 0.02 to 2,
    e=from 0 to 8, preferably from 0 to 5,
    f=from 0 to 10 and
    n=a number which is determined by the valency and frequency of the elements in formula (I) other than oxygen.

9. A process as claimed in claim 1, wherein the propene hourly space velocity on the fixed catalyst bed is $\geq 90$ l (STP)/l·h.

10. A process as claimed in claim 1, wherein the propene hourly space velocity on the fixed catalyst bed is $\geq 130$ l (STP)/l·h.

11. A process as claimed in claim 1, wherein the increase in the temperature of the fixed catalyst bed over time is carried out in such a way that the conversion of the propene in single pass of the reaction gas mixture through the fixed catalyst bed does not go below 93 mol %.

12. A process as claimed in claim 1, wherein the increase in the temperature of the fixed catalyst bed over time is carried out in such a way that the propene content in the product gas mixture does not exceed 10 000 ppm by weight.

13. A process as claimed in claim 1, wherein the starting reaction gas mixture contains from 7 to 15% by volume of propene.

\* \* \* \* \*